United States Patent [19]

Chibret

[11] Patent Number: 5,000,936
[45] Date of Patent: Mar. 19, 1991

[54] METHODS FOR LOCALLY-TREATING ALLERGIC DISORDERS WITH PHARMACEUTICAL PREPARATIONS CONTAINING N-ACETYL-ASPARTYL GLUTAMIC ACID OR ITS SALTS

[75] Inventor: Henri Chibret, Clermont Ferrand, France

[73] Assignee: THEA (Therapeutique et Applications) S.A., Clermont Ferrand, France

[21] Appl. No.: 169,905

[22] Filed: Mar. 18, 1988

Related U.S. Application Data

[63] Continuation-in-part of Ser. No. 86,209, Aug. 17, 1987, abandoned, which is a continuation of Ser. No. 613,638, May 24, 1984, abandoned.

[30] Foreign Application Priority Data

May 24, 1983 [FR]  France ................................. 83 08495

[51] Int. Cl.$^5$ ....................... A61K 37/02; A61K 9/06; A61K 9/12; A61K 9/08
[52] U.S. Cl. ..................................... 424/43; 424/400; 424/45; 514/19; 514/826; 514/885; 514/912; 514/947
[58] Field of Search ...................... 424/43, 40; 514/49, 514/912, 826, 885, 914, 947, 19

[56] References Cited

U.S. PATENT DOCUMENTS

| | | | |
|---|---|---|---|
| 3,658,995 | 4/1972 | Marchetti | 514/563 |
| 4,690,952 | 9/1987 | Kagatani | 514/2 |

FOREIGN PATENT DOCUMENTS 2257270  8/1975  France .

OTHER PUBLICATIONS

*Derwent Abst.*, 49726W/30, FERLUX, Oct. 1, 1974.
*Stedman's Medical Dictionary*, 23rd ed., The Williams and Wilkins Co., Baltimore, 1976, pp. 44, 62, 1446.
*The Merck Index*, 9th ed., Merch and Co. Inc., Rahway, N.J., 1976, entry No. 7498.
*Martindale Pharmacopeia*, A. Wade, ed., pp. 1445-1448, Martindale, U.K. (1982).
*The Merck Index*, 10th edition, M. Windholz et al., eds., p. 371, Merck Co., Inc. (1983).

*Primary Examiner*—F. T. Moezie
*Attorney, Agent, or Firm*—Millen, White & Zelano

[57] ABSTRACT

Pharmaceutical preparations with anti-allergic activity for local administration, which contains, a pharmaceutically acceptable salt of N-acetyl-(alpha, beta)-aspartyl glutamic acid in the form of ophthalmic preparations, nasal solutions, bronchial aerosols, and skin ointments.

10 Claims, No Drawings

METHODS FOR LOCALLY-TREATING ALLERGIC DISORDERS WITH PHARMACEUTICAL PREPARATIONS CONTAINING N-ACETYL-ASPARTYL GLUTAMIC ACID OR ITS SALTS

CROSS-REFERENCE TO RELATED APPLICATIONS

This application is a continuation-in-part of Ser. No. 086,209 filed on Aug. 17, 1987, which is a continuation of Ser. No. 613,638 filed on May 24, 1984, both of said applications now abandoned.

The present invention relates to new pharmaceutical compositions comprising: N-acetyl aspartyl (alpha, beta)-glutamic acid or its pharmaceutically acceptable salts which show surprising anti-allergic activity when administered locally, and it also relates to a new method for treating various medical disorders, such as conjunctivitis, rhinitis, bronchial asthma and dermatitis, when they have an allergic origin.

BACKGROUND OF THE INVENTION

Originally used in 1906 by Von Pirquet, the term "allergy" means a change in the reactions of the host when in contact with an "agent" called antigen or allergen. Nevertheless, the immunological mechanisms responsible for the signs and symptoms observed in allergic subjects are the normal body defense mechanisms common to all individuals. The difference is that, in allergic subjects, the body's immune response to antigens exceeds the aims of protection and becomes harmful for the subject himself. There is a very marked difference in the sensitivity of the immune response between the allergic subject and the non-allergic subject. For this reason, it is now generally preferred to use the terms hypersensitivity, rather than allergy, to describe the particular reactivity of the allergic subject in response to antigens. The allergic subject actually reacts to very small quantities of substances present in the environment, such as house dust and pollen, which, in the majority of people, do not provoke any particular reaction as they are minimally antigenic. These substances are not dangerous in themselves, but, in allergic subjects, they induce a series of immunological responses resulting in an episode of allergy, harmful for the host and for the tissues in which it develops.

Coombs and Gell have described four types of hypersensitivity reactions (Type I, II, III and IV) but in practice, these types do not necessarily occur separately from each other. The first three types are antibody (immunoglobulin) mediated, and the fourth is mediated primarily by specialized cells. In the recent years, "allergy" has become synonymous with Type I hypersensitivity in which the reactions are dependent on the specific triggering of immunoglobulin E (IgE) -sensitized mast cells by antigen resulting in the degranulation of mast cells and the release of pharmaceutically mediators of inflammation, such as histamine, leukotrienes and prostaglandins that cause vasodilatation, increased capillary permeability, smooth muscle contraction, and eosinophilia. Type I hypersensitivity may be followed by Type III hypersensitivity reaction when antigen meets antibody (primarily IgG and IgA) at body surfaces, for example in the lungs, the nose and eye, leading to the formation of antigen-antibody immune complexes which trigger a variety of inflammatory processes. They can interact with the complement system leading to the generation of anaphylatoxins C3a and C5a which have potential inflammatory effects and cause the release of vasoactive amines from the mast cells and basophils, thus increasing vascular permeability and attracting polymorphs. Activation of the complement system can also lead to the release of cytolytic components that are able to damage tissues. The mechanisms of hypersensitivity reaction involving mast cell degranulation and complement activation are described in detail in the following book; Immunology, I. Roitt (Sections 7, 19, 21 in particular).

The allergen present in the environment and capable of inducing allergic reactions in predisposed subjects are very diverse. The most usual ones are pollens, house dust, moulds, feather, animal furs and danders. Pollens are a very frequent cause of seasonal conjunctival and nasal allergic reactions ("hay fever") and bronchial allergy (asthma). House dust is principally responsible for perennial allergies which can affect the lungs (asthma), the nose (rhinitis) and the eye (conjunctivitis). The allergenic substances present in house dust are produced by microscopic mites belonging to the arthropod class. Moulds can also be responsible for allergic reactions since they are widely spread in nature and their spores are dispersed in great quantities by the wind. Animal furs and danders are among the most potent allergens. Domestic animals such as cats and dogs are frequent causes of respiratory allergies. The feathers contained in bedding are frequently accused of being responsible for allergic symptoms, however, it appears that in the great majority of cases, the allergen responsible is not the actual feather, but the Dermatophagoides mites which multiply in the feather used for beddings.

This list of the principal allergens is obviously not exhaustive. Any substance capable of triggering an immune response and participating in an immunological reaction is potentially allergenic. Countless numbers of substances are able to enter the body, induce a sensitization process and induce allergic reaction.

The reasons why certain subjects react to substances in the environment to which the majority of subjects remain insensitive remain largely unexplained. However, it is known that among the causative factors, genetic predisposition for allergy, environmental conditions (exposure to allergens) and local tissue factors play an important role.

The initial step in the sensitization process is the penetration of the allergen into the mucosa. Because of their exposure to the environment, the conjunctival, nasal, bronchial and mucosae are more frequently the site of sensitization processes than other mucous membranes.

The surface of the mucosa is endowed with mechanical defense mechanisms (mucus and mucociliary transport in the respiratory tract, lacrimal film in the eye) and immunological defense mechanisms (secretory immunoglobulin A) which normally constitute effective barriers to prevent the penetration of antigenic substances.

It is possible that allergic subjects present a fundamental or transient anomaly in these natural defenses, responsible for the penetration and persistence of allergens in the mucosa. In addition to this constitutional or acquired defect in the system of elimination of allergens, the immunological defense system in allergic subjects also has a particular predisposition for recognizing -as a result of a particularly accurate "memory"—very small quantities of an allergenic substance with which it has previously been in contact.

The anti-allergic drugs of the prior art may be classified in three categories:
coricosteroids which act on the cellular inflammation factors,
mast-cell degranulation inhibitors,
antihistamines.

SUMMARY OF THE INVENTION

A main object of the invention is to provide pharmaceutical compositions for use in treating locally disorders having allergic origin which show an activity as a mast cell degranulation inhibitor, preferably at least equivalent to sodium cromoglycate, which is considered to be the reference drug in this category. A further object of the invention is to provide such composition having in addition, an anticomplement activity which has been shown to be useful for treating allergic disorders since the complement system plays an important role in the mechanisms of inflammation, through the mediation of its anaphylatoxic and chematactic components (C3a, C4a, C5a) which have vasodilatory activity, increase capillary permeability and attract inflammatory cells.

According to this invention, it has been found that these two activities, which antagonize important phenomena in allergic inflammation, can be obtained from a single drug, comprising N-acetyl glutamic acid as an active compound. To our knowledge, this is the first time that an anti-allergic drug combines mast-cell degranulation and complement activation inhibitory effects.

N-acetyl-(alpha, beta)-aspartyl glutamic acid (NAAGA) is a compound which is already known per se, as indeed are several to its salts as described in the French Patent Application published under number 2,257,270. This patent specification discloses the use of salts of N-acetyl-(alpha, beta)-aspartyl glutamic acid (NAAGA) in the treatment of asthenic and/or shock states, on the basis of their pharmacological activities on the central nervous system. The compounds according to this prior art were used in pharmaceutical preparations to be administered by the oral (tablets, capsules, solutions) or intravenous or intramuscular routes (injectable solutes).

As the basis of the present invention, we have established that NAAGA and its salts possess mast cell degranulation inhibitory and anticomplement activities which has not been described before and are entirely distinct from the activities on the central nervous system described in the prior patent. We have also established that when given by their intended routes of administration (oral and parenteral) the preparation according to the prior art were not able to exert these pharmacological activities since, in these conditions, NAAGA is rapidly and extensively metabolized and therefore ineffective on mast cells and complement. On the contrary, when administered locally on the tissue or organ undergoing allergic phenomena, NAAGA was shown to be effective, provided its pharmaceutical form is suitable for this use, which was not the case for the preparation according to the prior art. Therefore we have invented a series of preparations containing NAAGA or salts of NAAGA as active compounds that are pharmaceutically acceptable according to the requirements usually formulated for local application on the eye (ophthalmic solutions, gels), in the nose (solutions and sprays), in the bronchi (aerosols), on the skin (ointments), for the treatment of allergic disorders affecting these organs. The use of NAAGA and its salts in therapy has been made possible by the fact that they are completely innocuous, locally as well as systemically.

N-Acetyl-(alpha, beta)-aspartyl glutamic acid and its salts are prepared according to methods known in themselves, such as those which have been described in the prior French Patent Application already mentioned (number 2,257,270). For instance, NAAGA sodium salt can be prepared according to Example 1 and used in solution of 50 % approximately, NAAGA can be used as prepared according to Example 7, and the hydrated magnesium salt can be used as obtained according to Example 6 of the same patent application, so as to prepare suitable pharmaceutical preparations according to the present invention, corresponding to the compositions described in the examples of the present application. In the preparations, NAAGA is advantageously in the form of metal salts, such as sodium, calcium and magnesium salts, or salts formed with aminoalcohols such as dimethylaminoethanol or dimethylaminoethanol, or of salts formed with basis aminoacids such as lysine. Generally, it is possible to use all pharmaceutically acceptable salts, formed with inorganic or organic bases, either alone or mixed together. They can, if appropriate, be used in hydrated form.

The preparations of the invention are useful for bringing about an anti-allergic effect by local application, in particular:
in the eye, in the treatment of allergic conjunctivitis,
in the nose, in the treatment of allergic rhinitis,
in the bronchi, in the treatment of asthma of allergic origin,
on the skin, in the treatment of dermatitis of allergic origin.

The invention will now be shown in greater detail in the following examples, which do not imply any limitation and which can vary according to the techniques of those skilled in the art, without thereby departing from the spirit of the invention.

In one preferred embodiment, the preparations according to the present invention can advantageously have the following general characteristics, when in liquid form:

1. The solution is isotonic, with an osmolality of between 250 and 350 mOsm, and preferably of the order of 300 m)sm, which can be adjusted by the addition of such compounds as sodium chloride.

2. Its pH is between 6.5 and 7.5, and preferably of the order of 7.0±0.3; it can be adjusted with HCl or NaOH for instance.

3. The solution is sterile, for example, such that it conforms to the "essai de stérilitépar filtration sur membrane" ("sterility essay by membrane filtration") in the French Pharmacopeia Edition X-V.2.I.I.

4. The solution contains a preservative in order to guarantee sterility of the solution during the period of its use (15 days minimum after opening the sterile bottle). This preservative can be, for example, a preservative chosen from among those conveniently used in solutions for local application (benzalkonium chloride, for example), or any one of the preservatives recommended by the French Pharmacopeia, such as p-hydroxy-benzoic acid or its esters, benzyl alcohol, thiomersal, chlorobutanol, etc.

5. Such a solution can show preferably a concentration between 1 and 6 %, expressed as weight of NAAGA acid with respect to the total weight of the solution. The solution may preferably contain a viscous agent, the role of which is to facilitate its spreading over the ocular and/or intranasal surfaces and to increase the duration of contact between the active substance and the conjunctival or nasal mucosa thereby enhancing the therapeutic action. By using a viscous agent with hydrophilic properties the solution is made able to mix with the lacrymal fluid or with the nasal mucus. Such an agent can be a cellulose derivative (e.g. H.P.M.C. or Hydroxy Propyl Methyl Cellulose, C.M.C. or Carboxy Methyl Cellulose, H.E.C. or Hydroxy Ethyl Cellulose, H.M.C. or Hydroxy Methyl Cellulose) or polyvinyl pyrrolidone or polyacrylic acid derivatives. Depending upon the viscous agent used and its concentration, the solutions may have viscosities in the range of 10 to 50 mPa.s.

EXAMPLE I.

Therapeutic methods for locally treating allergic conjunctivitis with ophthalmic preparations containing NAAGA Allergic conjunctivitis (as referred in MERCK MANUAL p. 235 Thirteenth Edition) of an acute or chronic form is usually part of a larger allergic syndrome such as hay fever, but may occur alone through direct contact with airborne substances such as pollen, fungus spores, various dusts, or animal danders. Itching is prominent and may be accompanied by excessive lacrimation. The conjunctiva is edematous and hyperemic. The cause is often suggested by the history and may be confirmed by skin testing. If allergic conjunctivitis is suspected but skin tests are equivocal, an ophthalmic challenge occasionally will be positive.

The therapeutic method according to the present example consists in administering drops of ophthalmic solutions or ophthalmic gels into the conjunctival "cul de sac" and/or on the eye-lid when the conjunctivitis is associated with blepharitis. These preparations are described hereafter.

EXAMPLE 1.1

| | |
|---|---|
| Magnesium salt of NAAGA | 3 g |
| (corresponding to 2 g of NAAGA acid) | |
| Benzalkonium chloride (preservative) | 0.01 g |
| Sodium chloride | 0.7 g |
| Hydrochloric acid | q.s. pH 7.3 |
| Purified water | q.s. 100 ml |

The osmolarity is 295 mOsm.

EXAMPLE I.2

| | |
|---|---|
| NAAGA | 4 g |
| Benzalkonium chloride | 0.01 g |
| sodium chloride | 0.21 g |
| Sodium hydroxide, NaOH, 0.1 N | q.s. pH 7.3 |
| (neutralizes the NAAGA acid) | |
| Purified water | q.s. 100 ml |

The osmolarity is 320 mOsm.

EXAMPLE I.3 and I.4

The composition in the examples is the same as in Example I.1., except that NAAGA is specifically either in alpha form (Example I.3), or in beta form (Example I.4). The alpha and beta forms can be separately isolated by using, for example, the method of preparation described in French Patent 1,477,573, while the method of preparation used in other examples normally leads to a mixture of the alpha and beta forms (65 % of alpha form and 35 % of beta form by weight).

EXAMPLE I.5

Another type of the present therapeutic method consists of administering NAAGA in the form of ophthalmic gels, in which NAAGA or its salts are present at concentrations between 0.5 % and 6 % and more advantageously between 1 and 3 %. One preferred composition is the following:

| | |
|---|---|
| NAAGA sodium salt (aqueous solution 50%) | 6 g |
| (equivalent to 2 g NAAGA acid form) | |
| Hydroxy propyl methyl cellulose | 1.5 g |
| (Metolose ® 90 SH 4000) | |
| Benzalkonium chloride | 0.01 g |
| Sodium chloride | 0.3 g |
| Hydrochloric acid | q.s. pH 7.0 |
| Purified water | q.s 100 ml |

The dosage for each of these compositions is advantageously 1 drop in each eye, 3 to 5 times per day, corresponding to a daily dosage per eye—as expressed in acid NAAGA equivalent—of 3 to 5 mg for Examples I.1., I.3., I.4., I.5. and 6 to 10 mg for Example I.2. One drop generally contain 30 to 40 μl of the solution, i.e. between.

Its should be emphasized here that the compositions previously disclosed in French patent specification 2 257 270 could certainly not be used in place of the compositions of the invention, since they are for different modes of administration and different dosage, either in unit dosage and daily dosage.

EXAMPLE II

Therapeutic methods for locally treating allergic rhinitis with intranasal medications containing NAAGA Allergic rhinitis (as referred in MERCK MANUAL p. 229. Thirteenth Edition) is a symptom complex including hay fever and perennial allergic rhinitis, characterized by seasonal or perennial sneezing, rhinorrhea, nasal congestion, pruritus, and often conjunctivitis and pharyngitis.

Hay fever, the acute seasonal form of allergic rhinitis, is generally induced by wind-borne pollens. The spring type is due to tree pollens (e.g., oak, elm, maple, alder, birch, cottonwood); the summer type, to grass pollens (e.g., Bermuda, timothy, sweet vernal, orchard, Johnson) and to weed pollens (e.g., sheep sorrel, English plantain); the fall type, to weed pollens (e.g., ragweed). Occasionally, seasonal hay fever is due primarily to airborne fungus spores.

The nose, roof of the mouth, pharynx, and eyes begin to itch gradually or abruptly after onset of the pollen season. Lacrimation, sneezing, and clear, watery nasal discharge accompany or soon follow the pruritus. The conjunctiva is infected, and the nasal mucous membranes are swollen and bluish red. Coughing and asthmatic wheezing may develop as the season progresses. Many eosinophils are present in the nasal mucus during the season.

The nature of the allergic process and even the responsible allergen is often suspected from the history. Diagnosis is confirmed by the above physical findings, skin tests, and the accompanying eosinophilia in blood or secretions.

In contrast to hay fever, symptoms of perennial rhinitis vary in severity (often unpredictably) throughout the year. Extranasal symptoms such as conjunctivitis are uncommon, but chronic nasal obstruction is often prominent and may extend to eustachian tube obstruction. The resultant hearing difficulty is particularly common in children. The diagnosis of allergic rhinitis is supported by a positive history of allergic disease, the characteristic bluish-red mucosa, numerous eosinophils in the nasal secretions, and positive skin tests (particularly to house dust, feathers, animal danders, or fungi, and occasionally to foods). Some patients have complicating sinus infections and nasal polyps.

The therapeutic method according to the present example consists in intranasally administering NAAGA solutions either in the form of drops or sprays delivered by mechanical pumps. These preparations are described hereafter:

EXAMPLE II.1

| | |
|---|---|
| Magnesium salt of NAAGA (corresponding to 2 g of NAAGA acid) | 3 g |
| Benzalkonium chloride | 0.01 g |
| Sodium chloride | 0.7 g |
| Hydrochloric acid | q.s. pH 6.8 |
| Purified water | q.s. 100 ml |

The osmolarity is 300 mOsm.

EXAMPLE II.2

| | |
|---|---|
| Magnesium salt of NAAGA (corresponding to 4 g of NAAGA acid) | 6 g |
| Benzalkonium chloride | 0.01 g |
| Sodium chloride | 0.2 g |
| Hydrochloric acid 0.1 N | q.s. pH 6.8 |
| Purified water | q.s. 100 ml |

The osmolarity is 300 mOsm.

The dosage is 1 to 2 sprayings in each nostril, 3 to 5 times per day, corresponding to a daily dosage per nostril - as expressed in acid NAAGA equivalent —of 3 to 30 mg for Example II.2 and of 1.5 to 15 mg for Example II.1.

EXAMPLE II.3

The formula is the same as the formula of the example II.2. to which we add a viscous agent in the amount of 2 g.

EXAMPLE III

Therapeutic methods for locally treating allergic bronchial asthma with preparations containing NAAGA Bronchial asthma (as referred in MERCK MANUAL p. 573. Thirteenth Edition) is a reversible airways obstruction not due to any other disease. Bronchial asthma can occur secondarily to a variety of stimuli. Persons whose asthma is precipitated only by allergenic exposure (most commonly airborne pollens and moulds, house dust, animal danders) and whose symptoms are IgE-mediated, are said to have allergic or "extrinsic asthma". By contrast, symptomatic episodes appear to be triggered only by nonallergenic factors *infection, irratants, emotional factors). These patients are said to have nonallergic or "intrinsic asthma". in many individuals, both allergenic and nonallergenic factors appear to play significant triggering roles.

Asthmatic attacks are characterized by narrowing of the large and small airways due to bronchial smooth muscle spasm, edema and inflammation in the bronchial mucosal wall, and tenacious mucus production resulting in decreased alveolar ventilation.

Individuals with asthma differ greatly in the frequency and degree of their symptoms. Some have only an occasional symptomatic episode, mild in degree and of brief duration, and otherwise entirely free of symptoms. Others have mild coughing and wheezing much of the time, punctuated by severe exacerbations of symptoms following exposure to known allergens, viral infections, exercise, or non specific irritants.

In more sever episodes, the patient may not be able to speak more than a few words at a time without having to stop for breath. Fatigue and severe distress are evident in the rapid, shallow, ineffectual respiratory movements. Cyanosis becomes evident as the attack worsens.

Examination of the blood and the sputum of a patient with asthma commonly shows eosinophila regardless of whether allergic factors can be shown to have an etiologic role in the disease. Blood eosinophilia is the rule.

The sputum in a patient with uncomplicated asthma is highly distinctive. Grossly, it is tenacious, rubbery, and whitish. In the presence of infection, particularly in adults, the sputum may be yellowish.

Pulmonary function test are valuable not only in differential diagnosis, but also in known asthmatics for assessing the degree of airway obstruction and disturbance in gas exchange, for measuring the airway response to inhaled allergens and chemicals such as histamine and methacholine (bronchial provacation testing).

Allergy skin tests help identify environmental allergens which may play an etiological role. Skin tests are customarily done to detect IgE antibody to inhalants (pollens, molds, epidermals, house dust) and other allergens suggested by the patient's history.

The clinical approach to an asthmatic patient should be to first exclude other distress that can present with cough and wheezing, and then identify and control exacerbating environmental or other factors. Drug therapy is an important therapeutic modality and enables most patients to lead relatively normal lives with few adverse drug effects.

There are four classes of drugs useful in the treatment of asthma. The first class is the beta-adrenergic agents. They cause bronchial smooth muscle relaxation and inhibition of mediator release, at least in part by stimulating the adenyl cyclase-cAMP system. The second class of drugs includes theophylline and its derivatives. These also cause bronchial smooth muscle relaxation and inhibition of mediator release. The third group of drugs is the corticosteroids. In addition to reducing edema and inflammation, they appear to increase the sensitivity of the beta-adrenergic receptor to catecholamines. Finally, disodium cromoglycate represents a new class of agents which appear to directly inhibit mediator release. In general, the adrenergic agents are most useful for treating the acute attack. Theophylline is a valuable adjunct to adrenergic drugs in the management of acute episodes. Because of their potentially dangerous long-term side effects, corticosteroids, while exceptionally effective, are withheld except for short term use until all other treatments have failed. Cromoglycate is primarily useful for maintenance therapy only and has no place in treatment of the acute attack.

NAAGA given via an aerosol —wet or dry—is effective in preventing allergen-induced asthma in sensitized asthmatics and therefore has a place in the treatment of asthma of allergic origin.

One preferred therapeutic method according to the present example consists in administering aerosols of NAAGA solutions as prepared as follows:

EXAMPLE III.1

| | |
|---|---|
| Magnesium salt of NAAGA (corresponding to 2 g of NAAGA acid) | 3 g |
| Benzalkonium chloride | 0.01 g |
| Sodium chloride | 0.7 g |
| Hydrochloric acid 0.1 N | q.s. pH 6.8 |
| Purified water | q.s 100 ml |

The daily preferred dosage is 30 to 50 ml aerolized that is to say 0.6 to 1 g of NAAGA acid.

EXAMPLE III.2

In this example, magnesium salt of NAAGA has been used as a micronized powder, the size of particles should be less than 5 micrometers. It has been mixed with isopropyl myristate as an emulsifier in order to improve the suspension of the product and avoid the agglomerate formation. FREON is the propellant.

| | |
|---|---|
| Magnesium salt of NAAGA | 2.68 g |
| Isopropyl myristate | 1.95 g |
| FREON 11/12 20:60 | q.s. 100 ml |

This composition will be conditioned into a pressurized vial with a device fitted with a valve which allows the delivering of a measured dose. A puff corresponds to 4 mg of NAAGA acid.

A daily preferred dose can comprise two puffs four times. That is equivalent to 32 mg of NAAGA Acid. Indeed, the ejected dose vary with the type of valve used and while the unit dosage is generally from 1 to 10 mg NAAGA, the dosage is preferably from 10 to 100 mg NAAGA.

EXAMPLE IV

Therapeutic methods for locally treating dermatitis of allergic origin with topical preparations containing NAAGA or its salts Dermatitis (also termed eczema) is a superficial inflammation of the skin, characterized by vesicles (when acute), redness, edema, crusting, scaling, and usually itching. Scratching or rubbing may lead to lichenification.

Two types of dermatitis are thought to involve hypersensitivity or allergic phenomena: contact dermatitis and atopic dermatitis.

Contact dermatitis is an acute or chronic inflammation, often sharply demarcated, produced by substances in contact with the skin.

Contact dermatitis may be caused by a Type IV delayed hypersensitivity reaction often due to ingredients in topical medications: antibiotics, anesthetics, and stabilizers. Other commonly implicated substances include plants, many potential sensitizers used in the manufacture of shoes and clothing, metal compounds, dyes, and cosmetics. Industrial agents capable of producing occupational dermatoses are almost innumerable. Contact dermatitis ranges from transient redness to severe swelling with bulla formation, itching and vesiculation are common. Any part of the skin that comes in contact with a sensitizing or irritating substance (e.g. ragweed pollen, insecticide spray) may be involved. Characteristically, the dermatitis is sharply limited to the site of contact at first; later it may spread to other areas. Continuing exposure to the causative agent or complications such as irritation from or allergy to a topical medication, excoriation, or infection may induce a chronic dermatitis. Since contact dermatitis may resemble other types of dermatitis, an allergen or irritant should be suspected as the cause or aggravating factor in any puzzling dermatitis. Characteristic skin changes and a history of exposure facilitate the diagnosis. Patch testing with a standard group of contact allergens may be helpful if questioning is fruitless.

Atopic dermatitis is a chronic, itching, superficial inflammation of the skin usually occurring in individuals with a personal or family history of allergic disorders (e.g. hay fever, rhinitis, asthma). Patients with atopic dermatitis usually have high serum levels of reaginic (IgE) antibodies and peripheral eosinophilia. Atopic dermatitis may begin in the first few months of life, with weeping, crusted lesions on the face, scalp, and extremities. In older children (or, uncommonly, in adults) it may take a more localized chronic form. The course is inpredictable. Although the dermatitis usually subsides by age 3 or 4 years, exacerbations and remissions frequently recur during childhood, adolescence, or adulthood. Itching is a constant feature. The consequent scratching and rubbing lead to an itch-scratch-rash-itch cycle. The dermatitis may become generalized. The frequent use of medications, proprietary or prescribed, exposes the atopic patient to many topical allergens, and contact dermatitis may aggravate and complicate the atopic dermatitis, as may the generally dry skin which is common in these patients. Diagnosis is entirely clinical and is based on the distribution of lesions, the long duration, and, often, a family history of allergy.

NAAGA given as an ointment has an anti-pruritic effect when itching is worst and protects the skin from persistent trauma and allows it to heal. It is less toxic than corticosteroids and thus better tolerated. The therapeutic method according to the present example consists in topically treating the lesions with an ointment containing NAAGA or its salts. The concentration may vary between 1 and 6 % by weight. The ointment contains a self emulsifying base which ensures the stability of the preparation: Tefose 63; an agent helping the diffusion and absorption of the Product: Labrafil M 2130 CS; an emollient agent helping the spreading and decreasing the fatty feeling: Propylene Glycol Dipelargonate; a fatty agent: thick paraffin oil, an emollient agent: Cetiol B, a moisturizing agent which maintains the skin humidity: glycerol and two preservatives agents: methyl p. hydroxybenzoate and propyl p. hydroxybenzoate.

With respect to the total composition, the ointment or skin cream preferably contains from 1 to 15 percent NAAGA salt by weight and is recommended for ointment of 1 sq.cm unit surface of skin with from 0.2 to 5 mg NAAGA.

In one preferred embodiment the ointment has the following composition:

| | |
|---|---|
| NAAGA sodium aqueous solution (50%) | 10 g |
| corresponding to NAAGA sodium salt | 5 g |
| Tefose 63* (Gattefosse) | 16 g |
| Labrafil M 2130 CS** (Gattefosse) | 2.7 g |
| Propylene Glycol Dipelargonate (Gattefosse) | 2 g |
| Thick Paraffin oil (Cooper) | 4 g |
| Cetiol B*** | 3 g |
| Glycerol (Cooper) | 5 g |
| Methyl p. hydroxybenzoate (Cooper) | 0.1 g |
| Propyl p. hydroxybenzoate (Cooper) | 0.05 g |
| Purified water | q.s. 100 |

* Saturated glycerides C10-C18 glycolyzed and polyoxyethylyzed
** Ethylene glycol and polyethylene glycol palmitostearates
*** Dibutyl adipate.

On example of the daily proposed dosage consists in three applications of an approximately two-centimeter cylinder of ointment on the area to be treated: Massage until complete penetration; this quantity of ointment is equivalent to 450 of ointment, that is to say 15 mg of NAAGA acid. This quantity is quite sufficient for treating a 15 cm square of skin.

It should be emphasized here that chromoglycate is not used in cream or ointment form.

EXAMPLE V

Studies of acute tolerance of the preparation according to Example II on ciliary movement

Introduction

These tolerance studies are necessary for all products intended for nasal or bronchial administration, as solutions, sprays or aerosols since whatever the therapeutic advantage of a product, it is important that it should not impair the ciliary movement, which is the motor component of the first "line of defence" of the airways constituted by the "muco-ciliary system", the role of which is to clean the respired air of numerous particulate pollutants, such as dusts, various allergens and microbial germs, which are suspended in the air.

Materials and methods

The technique used has been described under the name of microphotooscillography (L. G. CHEVANCE, J. F. LENNON: Etude des rythmes du battement ciliare (Study of rhythms of ciliary beating) Acta Otolaryng., 1970-70, 16-28)). In this study, guinea pigs or rabbits were used which were free of all clinical sign of infection of the airways. The animals are sacrificed, and then the nasal septum or trachea is dissected out. These tissues are placed in PBS survival medium and the superficial epithelium is removed by scraping, over an area of about 1 mm$^2$. This sample, which contains numerous ciliated cells in movement, is placed in an observation chamber under a special microscope equipped with a microphotoelectric system permitting the recording of ciliary beats in transillumination.

The measurement consists in recording the fluctuations in the light caused by the image, enlarged 500 times, of a cilium moving in front of the aperture of a diaphragm of suitable dimensions. After amplification, the fluctuations in light are recorded graphically.

Impairments of ciliary movement are translated as a decrease in the frequency of the ciliary beats. Such impairments depend, on the one hand, on the cellular toxicity inherent in the substances placed in contact with the ciliated cells and, on the other hand, on two physicochemical factor of fundamental; importance in the physiology of ciliary beating: the pH and osmolarity of the solutions.

Results

The results obtained are shown in Table 1, for the compositions of Example II.1. and II.2.

Specialist toxicologists recommend a criterion based on physiological data for evaluation of the cellular toxicity of a preparation intended for nasal, administration, namely that: "any solution (or suspension) is admissible which does not decrease by more than 50% the initial rate of ciliary beating after twenty minutes of contact". All the values obtained with the preparations according to Examples II.1. and II.2., after contact times which exceed 20 minutes, are, by a very wide margin, within the tolerance limits defined above.

Analogous results are obtained if the magnesium salt of NAAGA is replaced by the sodium salt prepared according to the patent application already mentioned, or by the calcium salt obtained according to Example 5 of the same patent application.

EXAMPLE VI

Effects of activated complement on the mucosa of the airways

Protective activity afforded by the preparations of Example II

Introduction

It has been demonstrated (M. Etievant, L. G. Chevance, Ann. Immunol. (Inst. Pasteur), 1980-131D, (13-42) that when the ciliated mucosa of the upper airways of sensitized animals is brought into the presence of the sensitizing allergen, there occur a very rapid arrest of the ciliary beats and very considerable cytological lesions at the level of the epithelial cells. It has been shown that this destruction is caused by the local activation of the complement, which leads to the release of cytolytic components.

From a physiopathological point of view, these complement-induced lesions of the respiratory mucosa play an important role in allergic diseases, by impairing ciliary movement and favoring the penetration and persistence of allergenic particles in the mucosa, thus enhancing the local inflammatory responses and, as indicated earlier, the activation of the complement releases mediators implicated in the symptoms of allergy. It is therefore beneficial for an anti-allergic drug to have—in addition to an inhibitory effect on mast-cell degranulation—an inhibitory effect on complement activation.

We have studied the anticomplement activity of the compositions according to Examples II.1. and II.2., as described hereafter.

Materials and methods

Rabbit tracheas are dissected out, then cut up so as to obtain several equal fragments of appropriate length (about 3 tracheal rings). These rings are opened, and then distributed in the following manner:
one of the rings, which serves as a control, is placed in Hanks survival medium,
each of the other rings is placed in 10 ml of each of the solutions to be tested, respectively that of Example II.1. and that of Example II.2.

After incubation at 37° C. for 15 minutes, the frequency of the ciliary beat is measured, then the preparations are immersed in 1 ml of autologous rabbit serum, containing complement.

To the different preparations is then added dextran sulfate (an activator of complement) at a concentration of 5 mg/ml, and the preparations are incubated for 20 minutes. After this incubation period, a measurement is made of the frequency of the ciliary beat by microphotooscillography. Cytological study, by electron microscopy, of the treated and control tracheal fragments were also performed.

Results

The results of the different trials carried out are shown in Table 2. They demonstrate that, in the control preparations, there is a complete arrest of the ciliary movement after 20 minutes of contact with the activated complement. Electron microscopy examination shows extensive destructions of the ciliated cells. It should be emphasized that, under the same experimental conditions, but with the serum not activated, ciliary beating is observed for several hours.

If, before incubating the mucosa in the activated serum, it is incubated for 20 minutes in the composition according to Examples II.1. and II.2., it is noted that after contact with the activated complement, the ciliary movement continues at a normal rate of beating and no or very minimal cytological lesions occur.

Conclusion

The compositions according to Examples II.1 and II.2. protect the respiratory mucosa very clearly and reproducibly against the cytological lesions induced by the local complement activation.

Analogous results are obtained when the magnesium salt of NAAGA is replaced by the salt formed with dimethyl-aminoethanol or diethylaminoethanol, prepared according to Example 11 or 12 of the prior patent application already mentioned, or by the salt formed with lysine, obtained according to Example 7 of this prior patent application.

Example VII

Activity of the compositions according to Example I in allergic conjunctivitis in the rabbit Method The experimental protocol has been established according to works by OKADA et al. (OKADA-SHIMADA, Invest. Ophthalmol. Vis. Sc. 1980, 19 2, 176–181).

The model of allergic conjunctivitis used consists in effecting a conjunctival immunization in rabbits by local injection of rabbit antibodies to bovine gammaglobulins. The conjunctivitis is then triggered by the inflammation of allergic origin thus provoked are observed as an increase in the weight of the conjunctiva, and as enhancement of the conjunctival capillary permeability to iodine-125 labeled rabbit serum albumin injected intravenously before the injection of the antigen.

Two hours after the injection of bovine gammaglobulins, the rabbits are sacrificed, and then the eyes are removed and the conjunctiva dissected out, weighed and submitted to radioactive counting.

Three parameters are recorded:
the weight of the conjunctiva,
the blood conjunctiva permeability index, evaluated as the ratio of the radioactivity of 1 mg of conjunctiva to that of 1 ml of blood,
the quantity of labeled serum albumin recovered in the conjunctiva.

To evaluate the protective effect of the preparation under investigation, several batches of six rabbits are formed, which receive 6 instillations of 2 eye-drops in each eye daily for 3.5 days before the injection of labeled serum albumin.

One batch of six normal rabbits, not tested and not subjected to provacation of the allergy, is also formed ("blank" batch), as well as a batch of six control rabbits receiving instillations of physiological serum before the triggering of the conjunctivitis ("conjunctivitis controls").

Results

The results obtained, in respect of the three parameters of conjunctival inflammation of allergic origin which were studied, are recorded in Table 3.

As inferred from these trials, it is seen that the eye drops according to the invention of Example I possess significant protective activity against conjunctival inflammation of allergic origin in the rabbit. Their activity is seen to be superior to that of sodium cromoglycate at 2 % concentration in an eye-drop, which was used as a reference drug. The results of the trials also bring out the importance of the choice of concentration, since the eye-drop according to Example I.1. diluted threefold must be considered inactive.

Furthermore, these results demonstrate that, at equal concentrations of NAAGA, the alpha and beta forms and their mixtures have an equivalent activity.

EXAMPLE VIII mast cell degranulation inhibiting activity of NAAGA on the nasal mucosa of the guinea pig Method The test is based on the determination by microscopy of the number of granulated mast cells per unit area in the nasal mucosa of the guinea pig, and on the study of the administration of a histamine releasing substance —48/80—on this number of mast cells. Guinea pigs receive in each nostril, twice daily during 3 days. 0.1 ml of the product under investigation, 15 minutes before the nasal instillation of 0.1 ml of 48/80 in solution at 2 % concentration; the animals are sacrificed 1 hour after the last instillation.

After sacrifice, the nasal mucosa is removed, then fixed and stained with toluidine blue to allow selective staining of the granulated mast cells. For each animal, the mast cells contained in 100 microscopic fields are counted by microscopy.

Results and conclusion

As shown in table 4, complete protection against mast cell degranulation is conferred by the preventive local treatment with the products of the invention based on NAAGA at 2 % or 4 % concentration. By way of comparison, sodium cromoglycate at 2 % concentration (commercial solution), used in the same experimental condition as the solutions based on NAAGA, shows a protective effect inferior to that of NAAGA by about 40 %.

The preparations according to EXAMPLE II.1. and II.2. of the invention, administered intravenously, thus possesses very considerable mast cell degranulation inhibitory activity at the level of the nasal mucosa of the guinea pig. Their effects are clearly superior to that of the reference drug, sodium cromoglycate.

EXAMPLE IX

Clinical study of the composition according to Example I.2 in the treatment of the allergic conjunctivitis The trial was performed in double blind. The objective was to determine the effects of the composition according to Example I.2.: an ophthalmic solution at 4 % concentration, on the ocular symptoms and inflammatory conjunctival signs of patients suffering from chronic allergic conjunctivitis, compared with the sodium cromoglycate in ophthalmic solution at 2 % concentration used in therapy.

The results of this comparative study concern 33 patients, of both sexes, who were distributed randomly into two groups:

received the composition according to Example I.2. during 2 weeks at the rate of 1 drop in each eye to be treated, 3 to 5 times daily. These patients then received sodium cromoglycate in eye-drops at 2 % concentration (commercial eye-drops) during two supplementary weeks and at the same dosage, 16 patients received the same eye-drops in the reverse order and for the same lengths of time.

The random assortment of the patients ensured good homogeneity in the distribution between the two treatment groups, not only in respect of the clinical characteristics, but also in respect of the duration of administration of the eye-drops under trial, and the use of concomitant treatments.

Conclusions

The results obtained demonstrate an improvement in the ocular symptoms in more than 65 % of the patients, with comparable results for both products. However the comparison of the two eye-drops according to the preferences expressed by the patients was clearly in favor of the composition of Example I.2. (67 % of the preferences in its favor, against 33 % in favor of cromoglycate).

EXAMPLE X

Clinical study of the composition according to Example III.1

This study concerned 6 subjects suffering from asthma through allergy to house dust, flour or pollen.

With these patients, the protective effect of the solution for bronchial aerosol at 2 % concentration, according to Example III.1., was investigated: 10 ml of this composition were aerolized for 10 minutes before performing a provocation test using the allergen responsible for the asthma in these patients.

The results of measuring the expiratory flow rates by spirometry (MEFR), and also the clinical signs of respiratory allergy after NAAGA +allergenic provocation, were compared in relation to a prior test of provocation in the same subjects, but without previous administration of NAAGA.

Table 5 summarizes the results obtained with these different patients.

A protection against the immediate and/or delayed broncho-constrictor reaction caused by inhalation of the allergen will be noted in 5 cases out of 6 (Nos. 1, 2, 3, 4 and 6).

EXAMPLE XI

Antiallergic effect of preparations according to Example IV by topical cutaneous application in the passive cutaneous anaphylaxis test (P.C.A.) in the rat

Introduction

In the present study we have used the P.C.A. test first described by Mota (Immunology, 1964, 7, 681–706) and further developed by Goose and Blair (Immunology, 1968, 16, 749–760) and other authors (Int. Arch. Allergy Appl. Immunology, 1980, 61, 19–27). P.C.A. is a form of experimental immediate local hypersensitivity. In passive anaphylaxis sensitization is transmitted to a new animal by injection of IgE-rich serum from a sensitized animal. This test allows qualitative and quantitative evaluation of antibodies involved in this reaction; in the present study, we sought to determine whether topical application of NAAGA could protect animals against cutaneous anaphylactic reactions.

Materials and methods (principle)

Injection of ovalbumin solution (OVA) with a bacterial adjuvant (*Bordetella pertussis*) leads to production of serum antibodies in the rat. This antiserum is then injected intradermally to another rat where it triggers an anaphylactic reaction upon exposure to intravenous OVA.

In the rat this reaction can be shown by the development of blue spots at the sites of titrated injection antiserum due to diffusion of Evans blue added to the OVA. The size of these spots varies as a function of the degree of anaphylactic reaction. Calculation of areas allows evaluation of intensity of the reaction.

The preparation according to Example IV is topically applied twice daily for 3 days on the sites of previous injections of antiserum to the back of the animals, massaging until complete penetration. Controls receive placebo ointment under the same conditions. A last application of ointment is done 2 hours before triggering injection of OVA. Thirty minutes after this injection, rats are sacrificed and the diameters of the spots are measured.

Results

Results are shown in table 6. The ointment according to Example IV produces significant ($p < 0.05$) inhibition of the cutaneous anaphylactic reaction.

It has already been indicated that the compositions of the examples and results reported have been given without any implied limitation. It will be noted in particular that, following the method of preparation of the compounds which has appeared preferable, the alpha and beta compounds are mixed together in the drug. However the invention can also be applied by using the compounds obtained specifically in the alpha and beta form.

Likewise, it would be possible to use any other type of NAAGA salt, formed with an inorganic or organic base, leading to a salt which was pharmaceutically acceptable for local administration.

EXAMPLE XII

Clinical study of the composition according to Example I.2 in the treatment of sub-acute and chronic atopic conjunctivitis Twenty seven patients suffering from sub-acute and chronic atopic conjunctivitis who were treated for at least one year on 2 % Cromoglycate eye-drops, were switched from Cromoglycate treatment to 4 % NAAGA eye-drops four times daily. Before and after two months treatment period with composition according to example I.2., the patients were checked objectively in order to score the severity of conjunctival livid hyperemia and the amount of exudate. Subjectively the patients were asked to assess the symptoms of itching, burning and photophobia. Objective and subjective assessments were scored by means of visual analog scales.

Statistical analysis of subjective and objective scores showed that a significant gain in treatment effect was obtained after changing the treatment regimen from Cromoglycate to the composition according to example I.2. The frequency of marginal objective and subjective control by Cromoglycate was reduced by composition according to Example I.2. from 33 % to 18 % and from 37 % to 22 % respectively.

EXAMPLE XIII

Clinical study of the composition according to example II.2 in the treatment of perennial allergic rhinitis The aim of the present study was to determine the efficacy and tolerance of the composition according to example II.2., in the treatment of allergic rhinitis. For this purpose, a double-blind trial was undertaken versus a reference drug: disodium Cromoglycate in a 2 % nasal solution.

The study involved 34 patients, suffering from perennial allergic rhinitis. Each patient was included in a cross-over treatment protocol, according to which the two drugs compared were administered successively during 2 treatment periods of 2 weeks each, at the dose of 2 sprays per nostril, 5 times per day.

Analysis of changes in symptoms of rhinitis and rhinoscopic signs during the 34 treatment periods with the composition according to example II.2. and the 33 treatment periods with Cromoglycate, showed that the composition according to example II.2. has a significantly superior action to Cromoglycate, regarding overall nasal symptomatology and, in particular, nasal obstruction. By contrast, there was no significant difference between the two types of treatment concerning rhinoscopic signs of rhinitis. Results of treatment were considered to be good in 81 % of patients with the composition according to example II.2. and 61 % of patients with Cromoglycate. Analysis of preference expressed by the physician, on a double-blind basis, for one or the other of the types of treatment compared, showed that the composition according to example II.2. was significantly more often preferred than Cromoglycate, in particular when the latter had been considered to be ineffective earlier. Nasal and systemic tolerance of the composition according to example II.2. and of Cromoglycate was good and no side-effects were seen. On the basis of the results obtained, it was therefore concluded that the nasal solution according to example II.2 is more effective than Cromoglycate against the symptoms of allergic rhinitis and that it is well tolerated.

TABLE 1

Study of acute tolerance on ciliary movement

| Product tested | Number of experiments | pH | Osmolarity (mOsm) | Animal tissue | Temperature (°C.) | Before PBS | After 20 min | After 40 min |
|---|---|---|---|---|---|---|---|---|
| NAAGA 2% (Example II.1) | 2 | 6.8 | 338 | Rabbit nasal mucosa, trachea | 37 | 680 | 420 | 380 |
|  |  |  |  |  | 21 | 320 | 260 | 260 |
| NAAGA 2% (Example II.1) | 3 | 6.9 | 348 | Guinea pig | 21 | 400 | 360 | 400 |
|  |  |  |  | Guinea pig | 21 | 500 | 480 | 400 |
|  |  |  |  |  | 21 | 360 | 360 | 400 |
| NAAGA 4% (Example II.2) | 3 | 6.8 | 300 | Guinea pig trachea | 21 | 320 | 220 | 200 |
|  |  |  |  |  | 21 | 340 | 280 | 280 |
|  |  |  |  |  | 21 | 360 | 440 | 440 |

TABLE 2

Protective effects against the action of activated complement

| Substances tested (concentration) | Experiment | Study of ciliary beating (cycles/min) Before activation of the complement | 20 min after activation of the complement | Electron microscopie study (SEM) After activation of the complement |
|---|---|---|---|---|
| Controls | 1 | 240 | In process of arrest | Complete destruction of the cilia |
| Solvent of the composition adjusted to 300 mOsm with preservative | 2 | 360 | Arrested | Complete destruction of the cilia |
|  | 3 | 420 | Arrested | Complete destruction of the cilia |
|  | 4 | 300 | Arrested | Complete destruction of the cilia |
|  | 5 | 220 | Arrested | Complete destruction of the cilia |
|  | 6 | 300 | Arrested | Complete destruction of the cilia |
|  | 7 | 320 | Arrested | Complete destruction of the cilia |
| NAAGA 2% (Ex. II.1) | 8 | 360 | 460 | Normal appearance of ciliation |
|  | 9 | 300 | 320 | Normal appearance of ciliation |
|  | 10 | 440 | 480 | Normal appearance of ciliation |
|  | 11 | 280 | 300 | Normal appearance of ciliation |
|  | 12 | 300 | 280 | Small damaged zone. Normal appearance of ciliation over |

TABLE 2-continued

Protective effects against the action of activated complement

| Substances tested (concentration) | Experiment | Study of ciliary beating (cycles/min) Before activation of the complement | 20 min after activation of the complement | Electron microscopie study (SEM) After activation of the complement |
|---|---|---|---|---|
| | 13 | 480 | 380 | majority of mucosa Normal appearance of ciliation. However small damaged zone present |
| | 14 | 280 | 300 | Normal appearance of ciliation except in 2 places with visible lesions |
| NAAGA 4% | 15 | 340 | 300 | Normal appearance of ciliation |
| (Ex. II.2.) | 16 | 400 | 380 | Normal appearance |
| | 17 | 360 | 420 | Ciliation substantially preserved |
| | 18 | 280 | 300 | Normal appearance except in one place where some lesions visible |

TABLE 3

Trial on allergic conjunctivitis

| Groups of rabbits | Quantity of serum albumin in the conjunctiva (in μg) | Blood-conjunctiva index (× 100) | Weight of the conjunctiva (in mg) |
|---|---|---|---|
| 1. "Blanks" (n = 12) (normal eyes) | 18.4 ± 5 | 2.53 ± 0.69 | 261 ± 58 |
| 2. Conjunctivitis controls (n = 12) | 51.6 ± 25 | 7.5 ± 3 | 664 ± 152 |
| 3. Na cromoglycate 2% (n = 12) (commercial eye-drops) | 34.5 ± 13.6 | 4.7 ± 1.8 | 411 ± 64 |
| 4. Magnesium salt of NAAGA 1%* (n = 12) | 54 ± 26 | 6.88 ± 3.73 | 465 ± 105 |
| 5. Magnesium salt of NAAGA 3% (n = 12) (Example I.1.) | 27.5 ± 9.3 | 3.75 ± 1.3 | 282 ± 93 |
| 6. NAAGA 4% (n = 12) (Example I.2) | 27.4 ± 6.5 | 3.74 ± 1.93 | 345 ± 59 |
| 7. Magnesium salt of -NAAGA 3% (n = 12) (Example I.3.) | 28.2 ± 6.2 | 3.96 ± 1.2 | 324 ± 52 |
| 8. Magnesium salt of β-NAAGA 3% (n = 12) (Example I.4.) | 27.9 ± 7.1 | 4.05 ± 1.7 | 311 ± 61 |
| 9. Sodium salt of NAAGA 3% (n = 12) (Example I.5.) | 25.4 ± 4.7 | 3.27 ± 0.9 | 298 ± 67 | n = number of eyes
* = prepared by ⅓ dilution of the 3% ophthalmic solution according to Example I.1. with physiological saline

TABLE 4

Mast cell degranulation of nasal mucosa of guinea pig by instillation of −48/80
Protective effects of NAAGA at 2% and 4% concentrations and of disodium cromoglycate

| Substances tested | Average number of granulated mast cells per microscopic field |
|---|---|
| Normal controls | 7.49 |
| | Instillation of 48/80 |
| Degranulated controls | 2.42 |
| NAAGA at 2% Example II.1. | 7.8 |
| NAAGA at 4% Example II.2. | 7.0 |
| Sodium cromoglycate at 20 mg/ml (commercial solution) | 4.6 |

TABLE 5

Clinical study - asthma

| Patient N° | Allergen | Test | % variation in MEFR after/before Immediate reaction | Delayed reaction | Clinical Immediate reaction | | Delayed reaction | |
|---|---|---|---|---|---|---|---|---|
| N° 1 | House dust | Control | | −19% | | | Rhin +++ | Sib ++ |
| REZ | | Ex. III.1 | Absent | −9% | Absent | | Rhin ++ | Sib 0 |
| N° 2 | Flour | Control | −15% | | Rhin +++ | Sib ++ | | |
| HAR | | Ex. III.1 | 0% | Absent | Rhin 0 | Sib 0 | Absent | |
| N° 3 | House dust | Control | −13% | −35% | Rhin + | Sib ++ | Rhin +++ | Sib +++ |
| REY | | Ex. III.1 | 0% | +23% | Rhin + | Sib ++ | Rhin 0 | Sib + |
| N° 4 | House dust | Control | −10% | | Rhin +++ | Sib ++ | Rhin ++ | Sib +++ |
| CHA | | Ex. III.1 | +8% | Absent | Rhin + | Sib ++ | Rhin 0 | Sib 0 |
| N° 5 | House dust | Control | −9% | | Rhin +++ | Sib ++ | | |
| GAR | | Ex. III.1 | +7% | Absent | Rhin + | Sib 0 | Absent | |
| N° 6 | Pollen | Control | −30% | −12% | Rhin ++ | Sib ++ | Rhin + | Sib + |

TABLE 5-continued

| | | | Clinical study - asthma | | | | | |
|---|---|---|---|---|---|---|---|---|
| | | | % variation in MEFR after/before | | Clinical | | | |
| Patient N° | Allergen | Test | Immediate reaction | Delayed reaction | Immediate reaction | | Delayed reaction | |
| OUH | | Ex. III.1 | −34% | +2% | Rhin + | Sib ++ | Rhin + | Sib + |

TABLE 6

| Study on passive cutaneous anaphylaxis | |
|---|---|
| | Mean area (mm²) of cutaneous spots |
| Preparation concording to Example IV (n = 6) | 90.5 (p < 0.05) |
| Placebo preparation (1) (n = 6) | 177.61 |

(1) same composition as in Example IV but without NAAGA
n: number of rats

I claim:

1. A method for treating allergic disorders by inhibiting mast cell degranulation in a patient comprising locally administering to said patient an anti-allergenically effect amount of a pharmaceutically acceptable salt of N-acetyl-(alpha, beta) aspartyl glutamic acid.

2. A method as claimed in claim 1 wherein said pharmaceutically acceptable salt is in an isotonic aqueous solution at a concentration of between 1 and 6%, expressed as weight of acid in relation to the total weight of said isotonic aqueous solution.

3. A method as claimed in claim 2 wherein said pharmaceutically acceptable salt is administered in the form of eye drops.

4. A method as claimed in claim 2 wherein said pharmaceutically acceptable salt is administered in the form of nose drops.

5. A method as claimed in claim 2 wherein said pharmaceutically acceptable salt is administered in the form of a bronchial aerosol.

6. A method as claimed in claim 1 wherein the allergic disorder is allergic ocular conjunctivitis.

7. A method as claimed in claim 1 wherein the allergic disorder is allergic rhinitis.

8. A method as claimed in claim 1 wherein the allergic disorder is asthma.

9. A method as claimed in claim 1 wherein said pharmaceutically acceptable salt is administered by application on the skin in the form of an ointment.

10. A spray composition for the treatment of allergic disorders by inhibiting mast cell granulation, said composition containing a propellant and an antiallergenically effective amount of an N-acetyl-($\alpha,\beta$) aspartyl glutamic acid salt.

* * * * *